United States Patent
Jia

(12) 
(10) Patent No.: US 7,867,751 B2
(45) Date of Patent: *Jan. 11, 2011

(54) PLASMID DNA ISOLATION

(75) Inventor: Xiyu Jia, Newport Beach, CA (US)

(73) Assignee: Zymo Research Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/603,855

(22) Filed: Nov. 21, 2006

(65) Prior Publication Data

US 2008/0020446 A1  Jan. 24, 2008

(51) Int. Cl.
*C12M 1/00* (2006.01)

(52) U.S. Cl. .................... 435/283.1; 435/975

(58) Field of Classification Search ........ None
See application file for complete search history.

(56) References Cited

U.S. PATENT DOCUMENTS

| | | | |
|---|---|---|---|
| 3,677,023 A | 7/1972 | Sun | |
| 5,075,430 A | 12/1991 | Little | |
| 5,160,412 A | 11/1992 | Berg | |
| 5,310,688 A | 5/1994 | Zale et al. | |
| 5,625,054 A | 4/1997 | Woodward | |
| 5,644,035 A | 7/1997 | Koths et al. | |
| 5,683,916 A | 11/1997 | Goffe et al. | |
| 5,693,785 A | 12/1997 | Woodward | |
| 5,808,041 A | 9/1998 | Padhye et al. | |
| 5,922,591 A * | 7/1999 | Anderson et al. | 435/287.2 |
| 6,277,648 B1 * | 8/2001 | Colpan | 436/177 |
| 6,281,349 B1 | 8/2001 | Pullybank | |
| 2003/0235839 A1 * | 12/2003 | McKernan et al. | 435/6 |
| 2005/0274924 A1 | 12/2005 | Horwath et al. | |
| 2006/0057738 A1 * | 3/2006 | Hall, Jr. | 436/177 |
| 2006/0286080 A1 | 12/2006 | Muller et al. | |
| 2007/0015169 A1 | 1/2007 | Jia | |

OTHER PUBLICATIONS

Birnboim and Dolly, A rapid alkaline extraction procedure for screening recombinant plasmid DNA, 1979, N.A.R., V.7 No. 6, 1513-1523.
Birnboim, 1983, Methods in Enzymology, V100, 243-255.
Volgelstein and Gillespie, Preparation and analytical purification of DNA from agarose, 1979, P.N.A.S., V. 76, No. 2, 615-619.
Clewell and Hellsenki, Properties of Deoxyribonucleic Acid-Protein Relaxation Complex, 1970, Biochemistry, V.9, No. 22, 4428-4440.
Volgestein and Gillespie, Preparation and analytical purification of Bacterial Plasmids, 1981, Analytical Biochemistry, 114, 193-197.
Marrko, et al., A procedure for the Large-Scale Isolation of Highly Purified Plasmid DNA Using Alkaline Extraction and Binding., Analytical Biochemistry, 121, 382-387 (1982).
Holmes, D. and Quigley, M., A Rapid Boiling Method for the Preparation of BActerial Plasmids, Analytical Biochemistry, 114, 193-197 (1981).
Sambrook and Russell, Chapter 1, Protocol 1, 2, and 3: Preperation of Plasmid DNA by Alkaline Lysis with SDS: Mini, Mldi, and Maxi, 2000, Cold Spring Harbor Laboratory Press.
Sambrook and Russell, Chapter 1, Protocol 7: Preperation of Plasmid DNA by Alkaline Lysis with SDS, 2000, Cold Spring Harbor Laboratory PresS.
Sambrook and Russell, Chapter 1, Protocol 9: Purification of Plasmid DNA by Chromatography, 2000, Cold Spring Harbor Laboratory Press.
Norimichi, T. et al., The Chemistry of Drying an Aqueous Solution of Salts, J. Phys. Chem. A 2009, 113, 12233-12242.

* cited by examiner

*Primary Examiner*—Christopher M. Babic
(74) *Attorney, Agent, or Firm*—Jonathan A Claypool

(57) ABSTRACT

The invention provides apparatus, reagents, and methods for rapidly isolating plasmid DNA from a bacterial alkaline lysate.

28 Claims, 9 Drawing Sheets

PLASMID DNA ISOLATION

CROSS-REFERENCE TO RELATED APPLICATIONS

This application claims priority to U.S. patent application Ser. No. 11/490,583 filed on Jul. 22, 2006 now abandoned which is herein incorporated by reference in its entirety.

FIELD OF THE INVENTION

The invention relates to methods, apparatus, and reagents for isolating plasmid or similar DNA from bacteria.

BACKGROUND

Plasmid DNA isolation (i.e., plasmid preps, mini-preps, rapid DNA preps, among other procedures) remains a repetitious and tedious laboratory task. Plasmid DNA isolation from bacteria has traditionally been performed using the "alkaline lysis" method, in which bacteria are resuspended in lysis buffer (P1), disrupted in a solution of NaOH and SDS (P2), neutralized in a solution containing sodium acetate (P3), and then subjected to centrifugation to sediment the flocculent cell debris containing denatured proteins and genomic DNA. Plasmid DNA remains in suspension, and is recovered by alcohol precipitation (see, e.g., Sambrook and Russell (2001) *Molecular Cloning*. Cold Spring Harbor Laboratory Press.).

Current popular methods of plasmid DNA preparation are based on the alkaline lysis method but use a spin-column to remove the debris from the alkaline lysate. The plasmid DNA is then recovered in a separate step, e.g., by alcohol precipitation of binding to a DNA-binding matrix. While the use of spin-column devices and kits have improved the speed and efficiency of plasmid preparation, the process continues to require multiple steps and fluid transfers. The need exists for more efficient methods, apparatus, and reagents for preparing plasmid DNA from bacteria.

SUMMARY OF THE INVENTION

The invention provides apparatus, methods, and reagents for isolating epigenomic DNA (e.g., plasmid DNA) from bacteria. One embodiment of the invention is a centrifuge/vacuum column apparatus (e.g., a spin-column) for isolating plasmid DNA from bacteria. The apparatus comprises a lysate filtration device having a mixing chamber for an alkaline lysate and a filtering medium in fluid contact with the mixing chamber. The lysate filtration device is in fluid contact with a DNA capture device having a DNA binding matrix. The lysate filtration device and the DNA capture device may be separate assemblies or a single assembly.

In operation, a bacterial alkaline lysate is provided in the mixing chamber of the apparatus. Upon applying an appropriate centrifugation or pressure force to the apparatus, plasmid DNA in the alkaline lysate flows though the filtering medium in the lysate filtration device to contact the DNA binding matrix in the DNA capture device. Plasmid DNA is captured on the DNA binding matrix. The DNA is then washed and eluted. The lysate filtration device may have a sealing cap, and the lysate filtration device and sealing cap may together form the mixing chamber.

A related embodiment of the invention is a spin-column apparatus for isolating plasmid DNA from a bacterial alkaline lysate comprising a mixing chamber for an alkaline lysate in fluid contact with first a filtering medium, and then a DNA binding matrix. As above, applying appropriate centrifugation or pressure force causes the plasmid DNA in the alkaline lysate to flow though the filtering medium and contact the DNA binding matrix. Plasmid DNA is thereby isolated on the DNA binding matrix in a single centrifugation or pressure step.

The lysate filtration device and the DNA capture device may be separate assemblies, which are assembled prior to use, or may be a single assembly, e.g., a single molded part, comprising a mixing chamber in fluid contact with a filtering medium and then a DNA binding matrix.

The invention further provides a method for isolating plasmid DNA from bacteria by alkaline lysis, the method comprising the steps of:

a) providing a bacterial suspension comprising bacteria having plasmid DNA;

b) adding a modified P2 reagent directly to the bacterial suspension, wherein the P2 reagent comprises an alcohol to reduce SDS precipitation;

c) adding a modified P3 reagent to the bacterial suspension to produce an alkaline lysate, wherein the modified reagent comprises a chaotropic agent;

d) removing cell debris from the alkaline lysate by filtration or centrifugation to obtain a lysate filtrate, and then capturing the plasmid DNA in the lysate filtrate using a DNA binding matrix, e) washing the plasmid DNA bound to the DNA-binding matrix; and f) eluting the plasmid DNA.

The cell debris may be removed by centrifugation and transferring the cleared lysate (herein lysate filtrate) to a DNA capture device or similar device having a DNA binding matrix. The cell debris may also be removed using a filtration apparatus and transferring the lysate filtrate to a DNA capture device or similar device having a DNA binding matrix.

In a preferred embodiment, step (d) is performed by filtering the alkaline lysate through a lysate filtration device having a filtering medium and capturing the plasmid DNA present in the lysate filtrate in a DNA capture device having a DNA binding matrix, wherein the filtering and capturing are performed using a single centrifugation or pressure step. The lysate filtration device and DNA capture device may be discrete components or a single assembly, i.e., a combined DNA isolation apparatus.

The invention further provides modified P2 and P3 reagents for use in methods of alkaline lysis, which are not limited to the methods and apparatus of the present invention. Where the modified P2 reagent is a liquid, it comprises alcohol to reduce SDS precipitation. Examples of suitable alcohols include isopropanol, 1-propanol, and ethanol. Where the modified P3 reagent is a liquid it comprises a chaotropic agent, and preferably potassium chloride. Where the modified P3 reagent is a solid, it further comprises a solid acid. Alkaline lysis may be performed using liquid, solid, or immobilized P2 or P3 reagents. Alkaline lysis may be performed directly in the mixing chamber or in a separate vessel (e.g., a centrifuge tube), wherein the resulting alkaline lysate is transferred to the mixing chamber.

The apparatus may be adapted for use with a centrifuge (e.g. a microfuge), vacuum manifold, or a related device. In some embodiments the spin-column is part of a multi-well strip (e.g., an 8-well strip) or is provided in multi-well (e.g., a 24, 48, 96, or 384-well plate) or other high throughput device/format. In other embodiments, a larger lysate filtration device and DNA capture device is used to isolate a greater quantity of plasmid DNA, as in the case of large-scale plasmid preparations (including so-called "midipreps" and "maxipreps").

The invention further provides kits of parts comprising an apparatus and/or reagents of the invention.

BRIEF DESCRIPTION OF THE DRAWINGS

FIGS. 7D and 7E show further embodiments of the invention, wherein the filtering medium and the DNA binding matrix are in a combined DNA isolation assembly, in a form more suitable for multi-well formats and high-throughput screening.

DETAILED DESCRIPTION OF THE INVENTION

Figure 1:
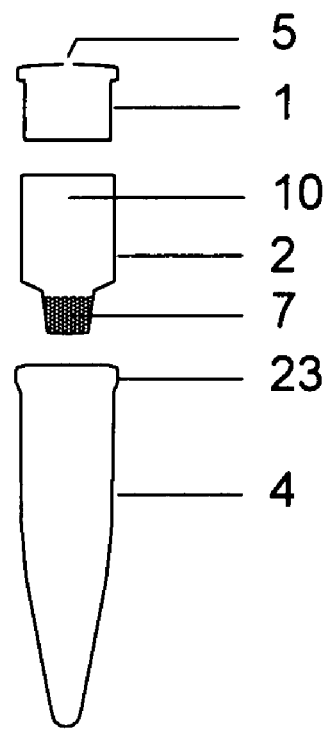
FIG. 1: Drawing depicting an embodiment of a lysate filtration device.

This invention provides methods, apparatus and reagents for rapidly isolating plasmid and similar epimeric forms of DNA from bacteria. One aspect of the invention features a centrifuge/vacuum column apparatus (e.g., a "spin-column" apparatus) for isolating plasmid DNA from bacterial suspensions. The apparatus comprises a mixing chamber in fluid contact with first a filtering medium and then a DNA binding matrix. Upon subjecting the apparatus of the invention to centrifugation, the alkaline lysate passes through the filtering medium to remove bacterial debris, and the resulting alkaline lysate filtrate contacts the DNA-binding matrix. As a result, DNA is isolated from an alkaline lysate in a single centrifugation step. The apparatus of the invention can also be used with a positive or negative pressure source to cause the alkaline lysate to flow in the direction of the DNA binding matrix.

The invention further provides modified P2 and P3 reagents for use with the apparatus of the invention to maximize plasmid isolation. In one embodiment, the P2 reagent is a more concentrated than a conventional P2 reagent, made possible by the inclusion of an alcohol (e.g., isopropanol, ethanol, or 1-propanol). The concentrated P2 reagent can be added directly to bacteria, eliminating the need to first concentrate the bacterial suspension (e.g., recover a bacterial pellet and resuspend the pellet in P1). The use of a smaller volume of P2 allows the use of a larger volume of bacterial suspension in the same total volume. The modified P3 reagent comprises a chaotropic agent to promote the binding of DNA to the DNA binding matrix. Preferred P3 reagents also comprise potassium chloride.

Some or all the steps of alkaline lysis may be performed directly in the mixing chamber. For example, the bacterial suspension may be added to the mixing chamber, and then P2 and P3 reagents are sequentially added to affect alkaline lysis. Alternatively, the P2 reagent is added to bacteria (or a bacterial suspension) and the solution is transferred to the mixing chamber where the P3 reagent is added. As another alternative, P2 and P3 reagents are sequentially added to bacterial suspension, and then the resulting suspension is transferred to the mixing chamber. In some embodiments, the P2 and/or P3 reagents are provided in the mixing chamber as part of the apparatus of the invention. Liquid, immobilized, or solid P2 and/or P3 reagents can be used with the invention.

Once the alkaline lysate is present in the mixing chamber, plasmid or similar DNA is isolated upon centrifugation or applying pressure to the apparatus. Debris from the alkaline lysate is filtered by the filtering medium, while plasmid DNA passes through the filtering medium and is bound by the DNA binding matrix.

In one embodiment, the apparatus comprises a lysate filtration device having a mixing chamber and filtering medium in fluid contact with the mixing chamber. This lysate filtration device is in fluid connection with a DNA capture device having a DNA binding matrix. In another embodiment, the lysate filtration comprising the filtering medium and the DNA capture device comprising the DNA binding matrix are a single assembly (i.e., a single part or component), herein referred to as a combined DNA isolation apparatus. The combined DNA isolation apparatus may be assembled from smaller parts or molded as a single assembly.

The invention improves on current apparatus and methods in several ways. It allows the use of a bacterial culture/suspension directly. There is no need to concentrate the bacteria by centrifugation or filtration. There is no need to remove the bacterial culture medium. In some embodiments, a modified P2 reagent is added directly to the bacterial culture, eliminating the need for a P1 reagent. The entire plasmid preparation process is performed without a pellet of bacteria or bacterial debris.

A. The Lysate Filtration Device

The present invention is best understood with the aid of the accompanying Figures. Referring to FIG. 1, the invention provides a lysate filtration apparatus based on a spin-column. The apparatus comprises a lysate filtration device 2 having filtering medium (i.e., a filter) 7 and optionally a sealing cap 1 to reduce spillage from the resulting interior space, herein referred to as the mixing chamber 10. The mixing chamber is the combination of the enclosed volume of the filtering device 2 and the enclosed volume of the cap 1, either of which volumes can readily be adjusted. A centrifuge tube 4 may be provided to collect lysate filtrate following centrifugation. In preferred embodiments, the lysate filtration device 2 is in fluid contact with a DNA capture device, as shown below. A non-air-tight sealing cap provides sufficient venting during centrifugation and fluid movement through the filter 7. Alternatively, an air vent 5 may be provided or air may enter through the filter.

Figure 2:
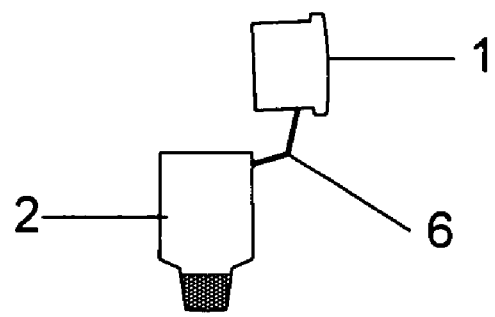
FIG. 2: Drawing depicting an embodiment of a lysate filtration device having a hinged sealing cap.

The lysate filtration device 2 and the sealing cap 1 may be a single assembly or separate components that come together at a sealing surface (not shown) to produce a mixing chamber 10 suitable for containing a cell suspension. The sealing cap 1 and lysate filtration device 2 may be attached via a flexible hinge 6, as shown in FIG. 2. The sealing cap 1 may have a substantial volume, thereby increasing the volume of the resulting mixing chamber 10.

In some embodiments of the invention, P2 and/or P3 reagents are provided in (i.e., disposed in or localized to) the mixing chamber 10. There are numerous embodiments of the invention with respect to the arrangement of the P2 and P3 reagents in the mixing chamber 10. Some of these P2 and P3 reagent arrangements work best with at least one solid or immobilized reagent. Solid or immobilized reagents should remain substantially localized within the mixing chamber during shipping of the apparatus to end-users. Some arrangements work with at least one liquid P2 and/or P3 reagent, or even liquid P2 and P3 reagents. In the case of liquid reagents, the end-user may be required to dispense the reagents into the appropriate part of the mixing chamber prior to introducing the bacterial suspension into the mixing chamber. Solid or immobilized reagents are more easily localized to a portion of the mixing chamber during transport and storage.

Figure 3:
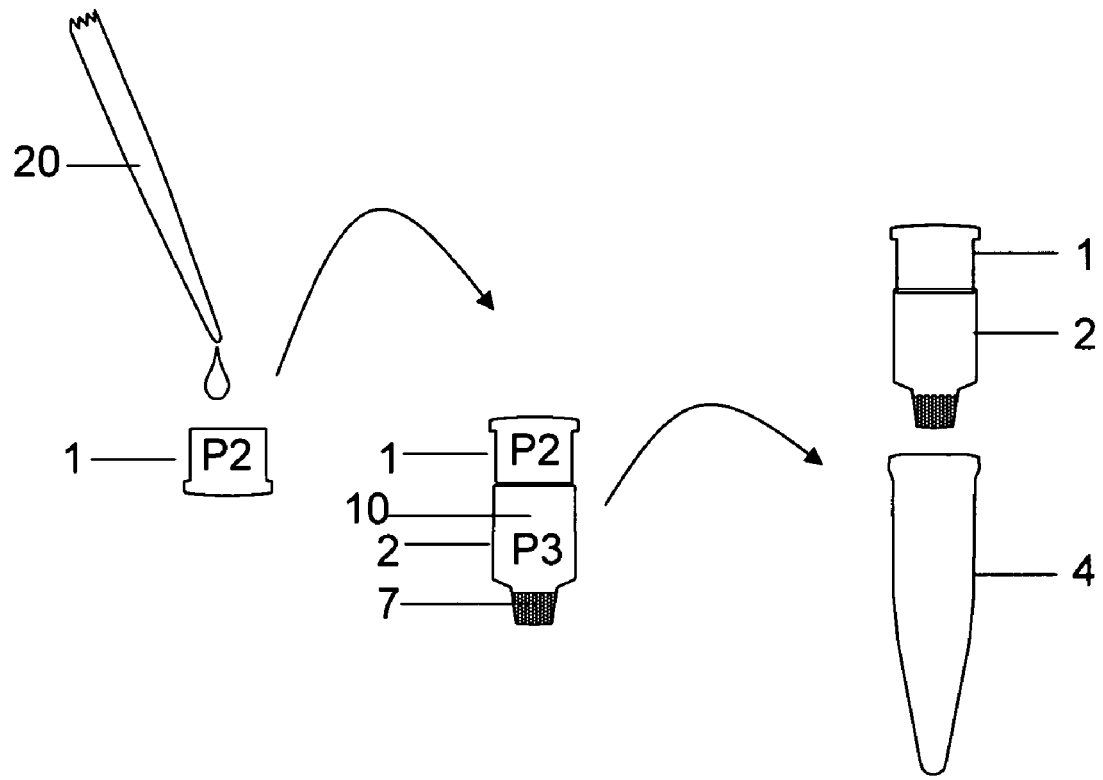
FIG. 3: Diagram depicting an embodiment of the invention in which P2 is provided in the sealing cap and P3 is provided in the lysate filtration device.

In a particular embodiment of the invention, the bacterial suspension is introduced (e.g., using a pipeting device 20) to the sealing cap 1, in which a P2 reagent is provided (FIG. 3). Following incubation, the sealing cap 1 is closed on the lysate filtration device 2 comprising a P3 reagent, creating a mixing chamber 10. The contents of the mixing chamber 10 can be mixed by inversion or other means, so long as the sealing cap 1 remains closed on the filter device 2 and the bacterial suspension remains confined.

Figure 4:
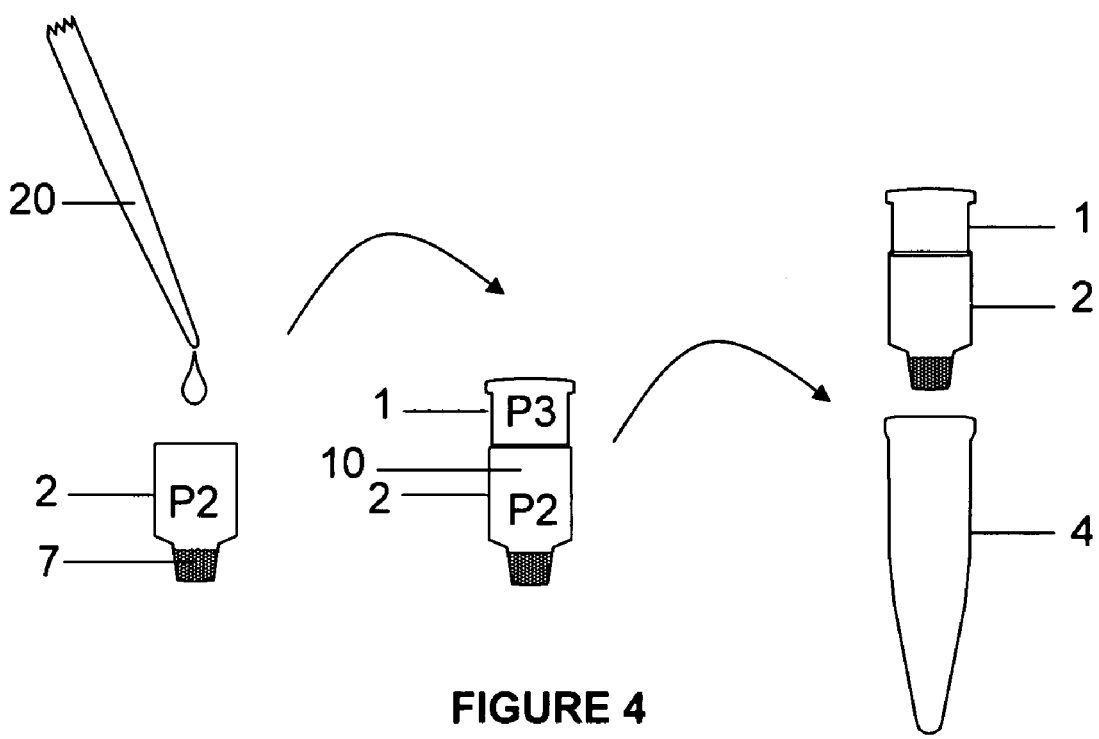
FIG. 4: Diagram depicting an embodiment of the invention in which P2 is provided in the lysate filtration device and P3 is provided in the sealing cap.

In another particular embodiment, a P2 reagent is provided in the lysate filtration device 2 and a P3 reagent is provided in the sealing cap 1 (FIG. 4). In such embodiments, the bacterial suspension is added to the lysate filtration device 2 to first contact the P2 reagent. After a few seconds of incubation, the sealing cap 1, in which the P3 reagents is provided, is closed and the contents of the mixing chamber 10 are mixed.

Figure 5:
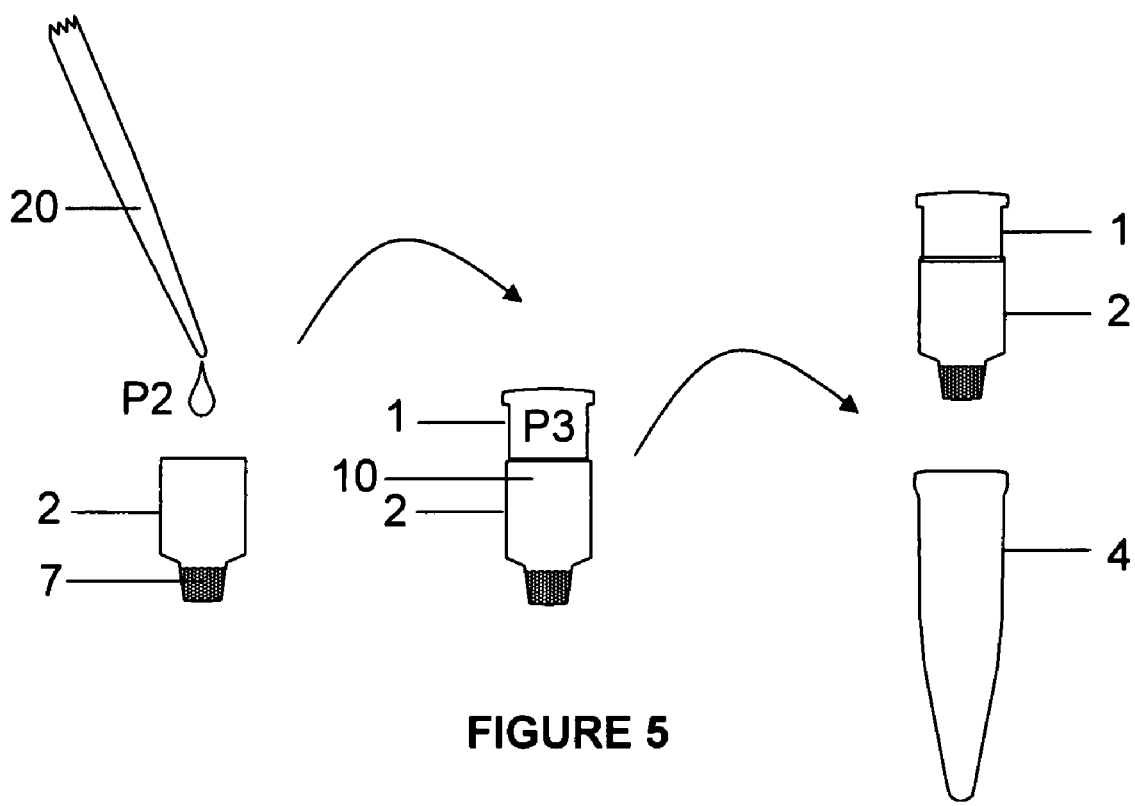
FIG. 5: Diagram depicting an embodiment of the invention in which P2 is provided in liquid form and P3 is provided in the sealing cap.

In another embodiment of the invention, P3 is provided in the mixing chamber 10 and P2 is added to the bacterial suspension in a separate vessel. In a preferred embodiment, P3 is provided as a solid or immobilized form in the mixing chamber, as illustrated in FIG. 5. According to this embodiment, a cell suspension is combined with a liquid P2 reagent, and the resulting mixture is added to the P3 reagent. Alternatively, the cell suspension and P2 are separately added to the mixing chamber 10. The P3 reagent may be provided in the sealing cap 1 (as shown in FIG. 5) or in the lysate filtration device 2. The P2 reagent should be well mixed with the bacterial suspension before the suspension contacts P3.

Figure 8:
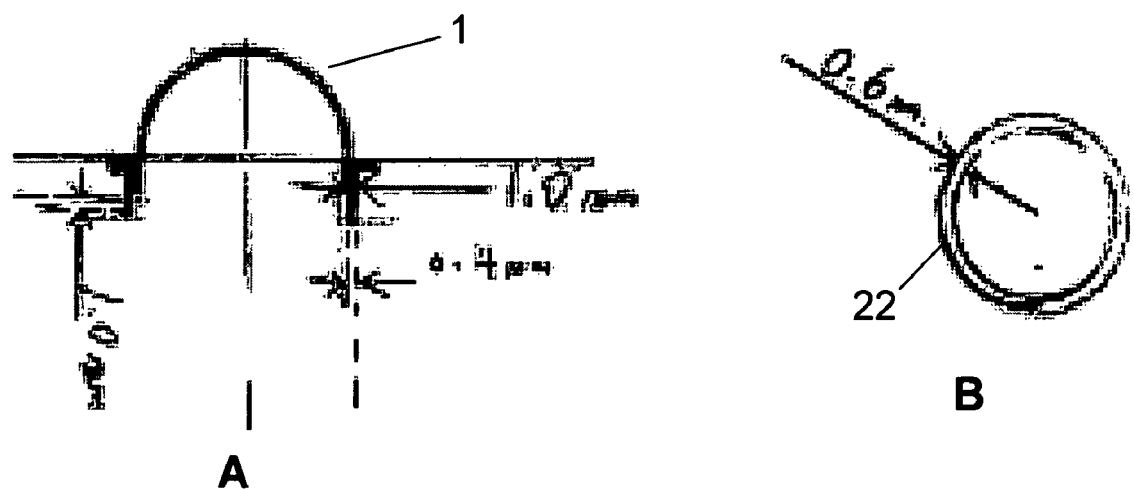
FIG. 8: Drawing depicting a preferred embodiment of the sealing cap having a groove (shown in A) to accept an internal ring (B) for retaining a water-soluble film (not shown).

Solid and immobilized forms of P2 and P3 reagents include solid (e.g., dry crystal or powder forms) or semi-solid forms (e.g., formulations comprising binders, gums, gels, dissolving matrices, and the like). The solid or semi-solid P2 or P3 reagents are immobilized (i.e., restricted, confined, or localized to a portion of the mixing chamber) by virtue of their solid or semi-solid form and/or immobilized in or behind water-soluble films, barriers, or packages and/or physical barriers. For example, FIG. 8 shows an embodiment of the sealing cap for use with solid or immobilized reagents (dimensions in mm). The ring 22 shown in FIG. 8B fits into the groove on the bottom (open end) of the cap 1 (FIG. 8A) for holding in place a circular sheet of water-soluble film for retaining a solid or immobilized P2 or P3 reagent. Examples of suitable films are provided herein.

B. DNA Capture Device

Figure 6:
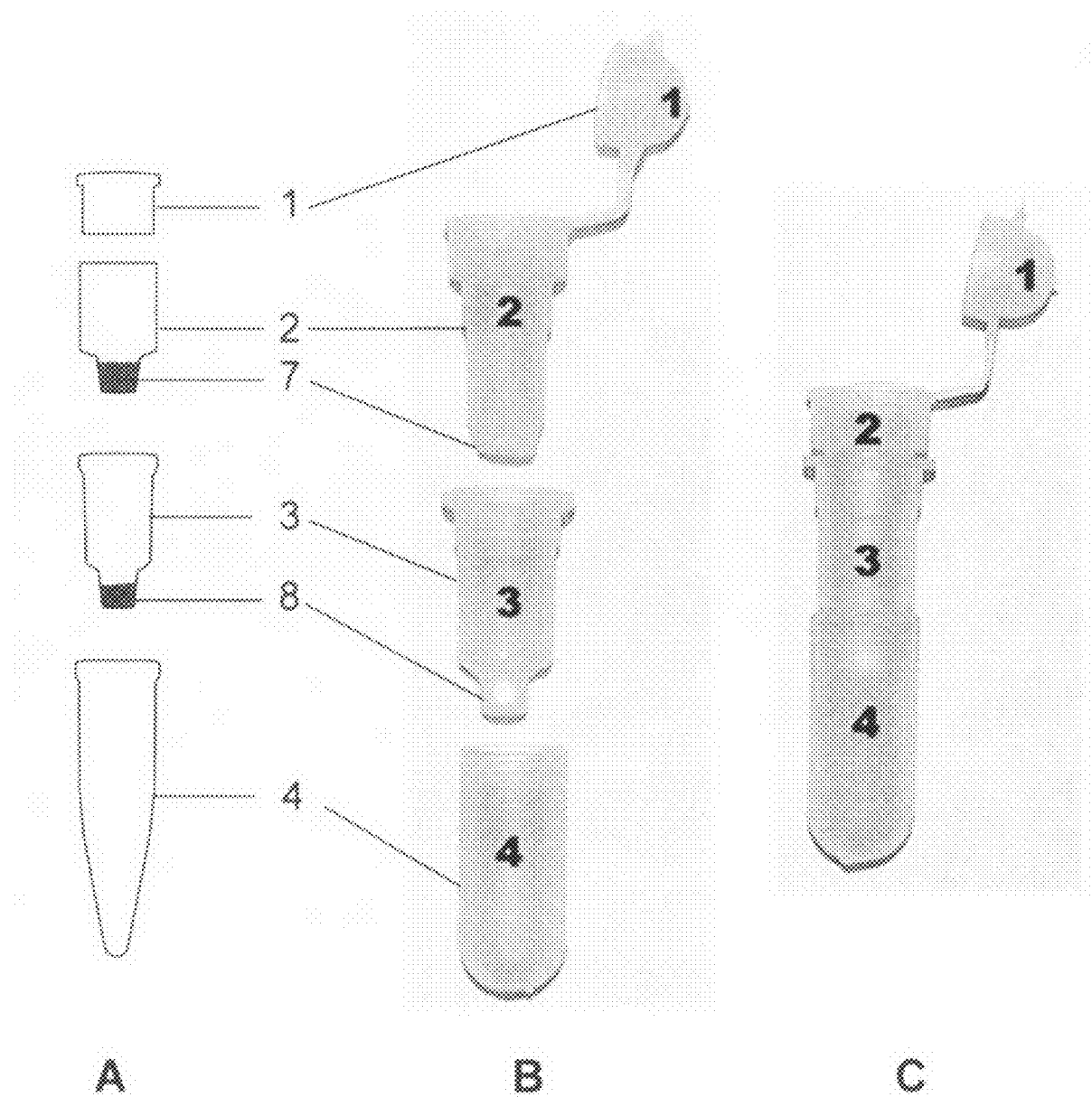
FIG. 6: Diagram and photograph depicting a spin-column embodiment of the invention. The sealing cap, lysate filtration device, DNA capture device, and centrifuge tube are numbered in the photograph.

In preferred embodiments of the method and apparatus, a spin-column lysate filtration device 2 is combined with a DNA capture device 3 to produce a single-centrifugation-step (or single pressure event) plasmid DNA isolation apparatus. An example of this embodiment of the invention is shown in FIG. 6. Following incubation in a P2 reagent followed by a P3 reagent, the alkaline lysate is subjected to centrifugation or pressure. The alkaline lysate passes through the filtering medium 7 producing a lysate filtrate which includes the plasmid DNA. The lysate filtrate contacts a DNA binding matrix 8 (e.g., a DNA-binding filter, such as a silicon matrix made from WHATMAN type C and F glass fibers) in the DNA capture device 3. The plasmid-depleted lysate filtrate passes through to the centrifuge tube 4 (or in other embodiments, to a waste bottle or vacuum trap).

The plasmid DNA is washed/rinsed on the DNA-binding filter 8 using, e.g., an ethanol-containing wash solution such as 75% ethanol with 5 mM Tris-HCl, pH 7.4. The plasmid DNA may be eluted from the DNA binding matrix 8 in an appropriate aqueous buffer (e.g., TE or water) for immediate use. The isolated DNA is sufficiently pure for most applications, but may be further processed to improve purity. Additional processing includes but is not limited to treatment with a chaotropic agent treatment and alcohol (e.g., ethanol, isopropanol, and/or butanol) precipitation followed by binding the DNA to a solid matrix (e.g., glass fibers or beads) to remove any contaminants.

Figure 12:
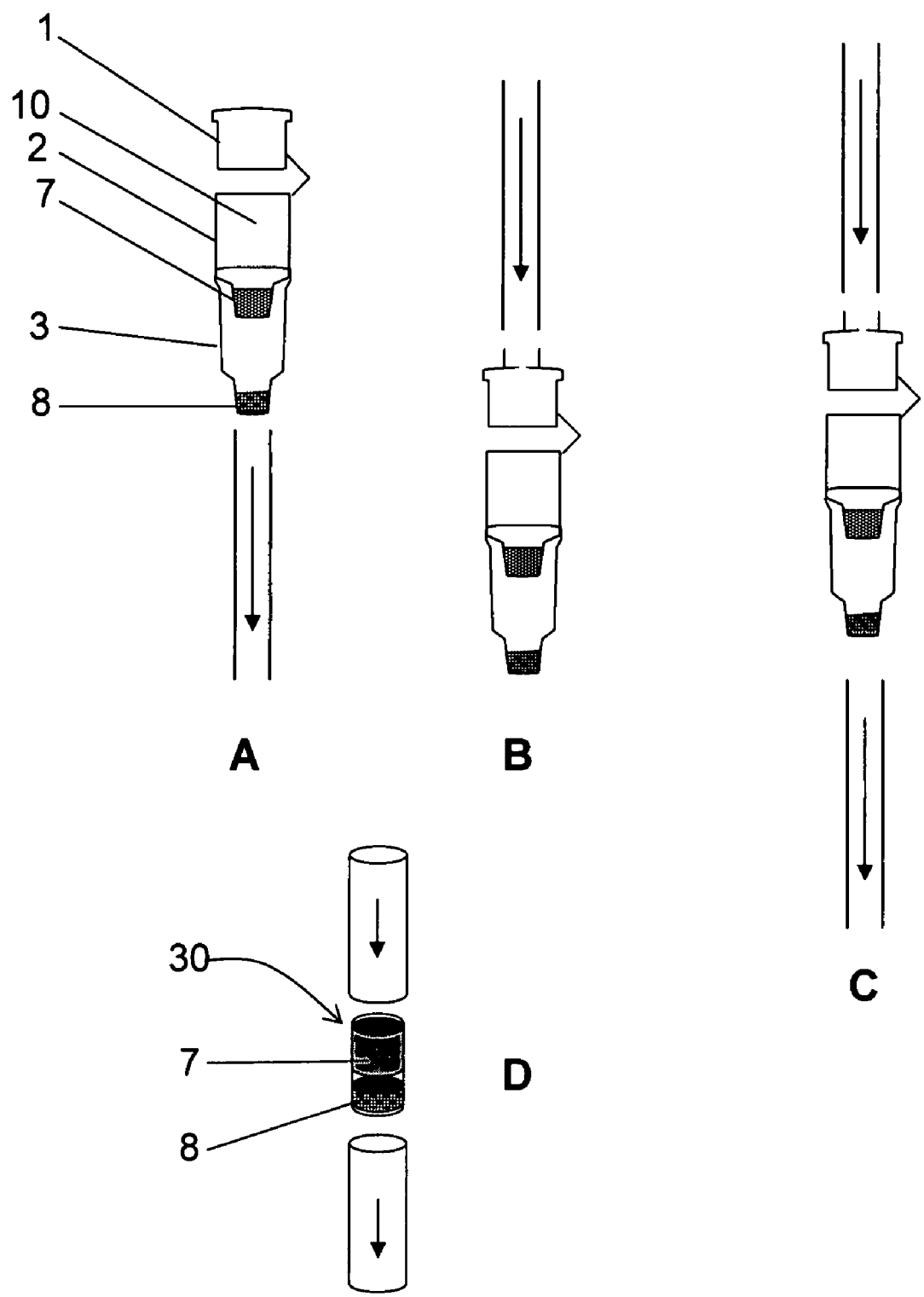
FIG. 12: Diagram depicting different embodiments of the invention relating to the use of positive of negative pressure force to cause the DNA in the alkaline lysate to flow in the direction the DNA binding matrix. Flow is indicated by arrows. (A) Embodiment of the invention for use with a vacuum source. (B) Embodiment of the invention for use with a positive pressure source. (C) In-line embodiment of the invention for use with positive and/or negative pressure. (D) Embodiment of the invention for multi-well applications or arrays

In some embodiments, the DNA-capture device is adapted to fit in or on a centrifuge tube. It may be desirable to use a centrifuge tube 4 that lacks a lip 23 as shown in FIG. 1. This allows the assembled apparatus (e.g., as shown in FIG. 6C) to be positioned lower in the rotor to avoid interferences with the rotor cap or centrifuge lid. In other embodiments, the apparatus is adapted for use with a positive of negative pressure source, as shown in FIG. 12.

Figure 9:
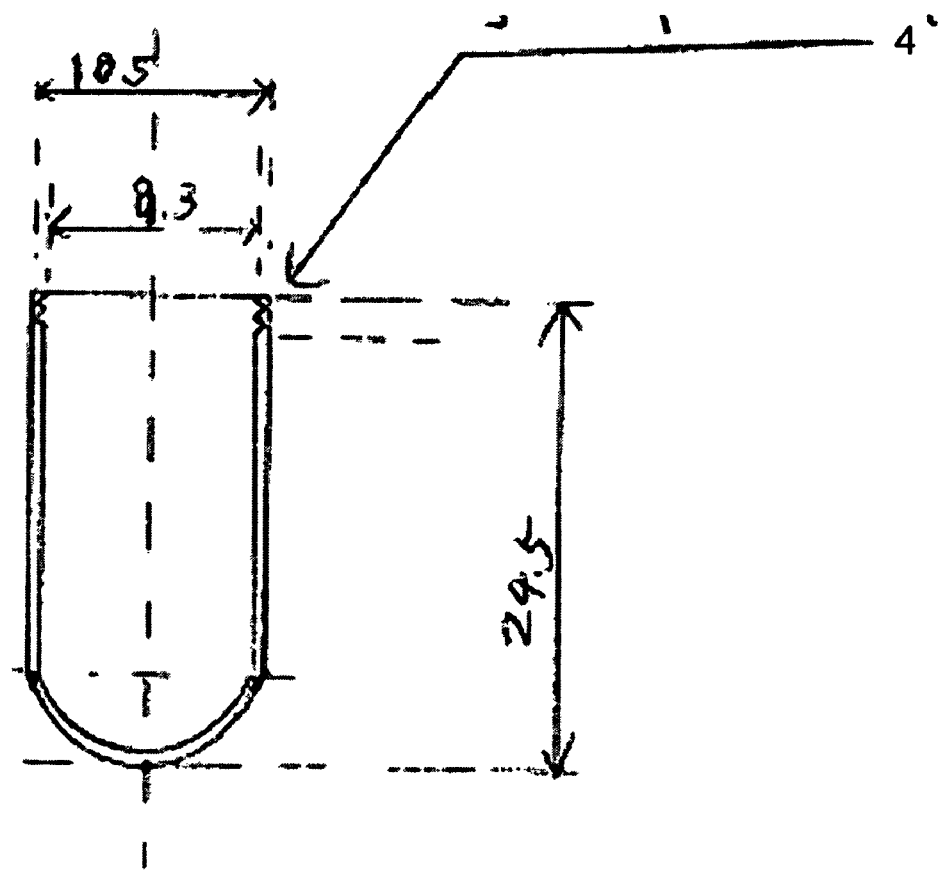
FIG. 9: Drawing depicting a particular embodiment of the centrifuge tube for use with the device shown in FIG. 6.
Figure 10:
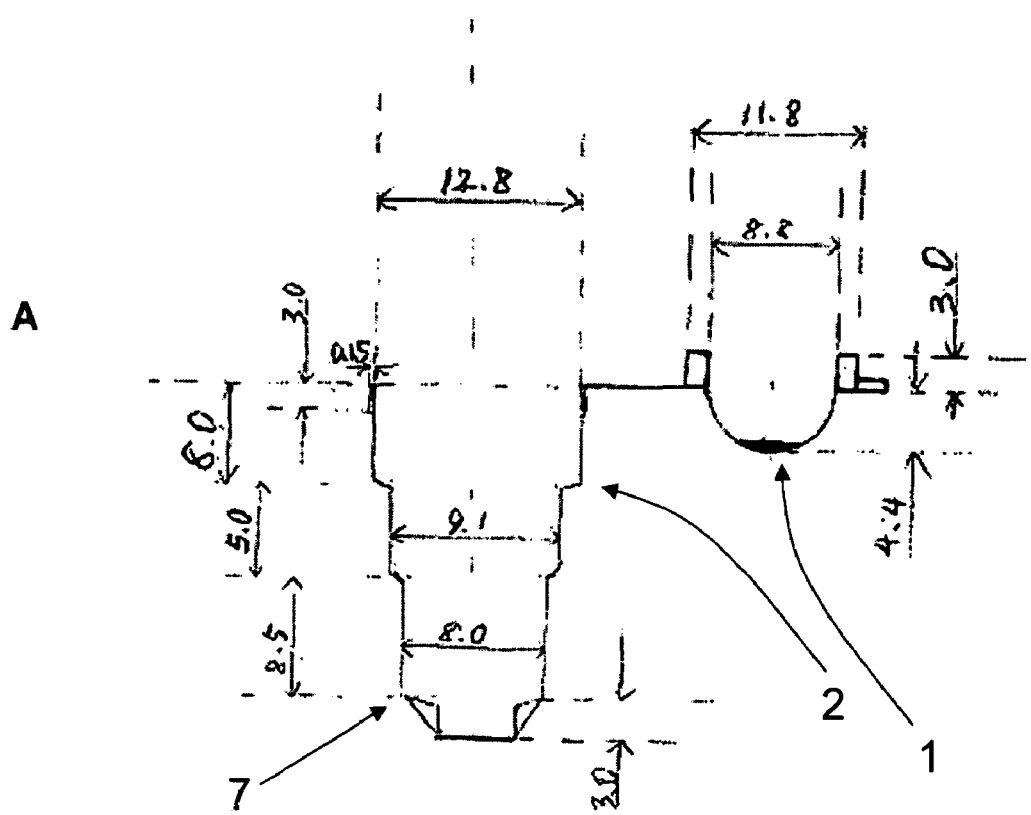
FIG. 10: Drawing depicting a particular embodiment of the lysate filtration device (A) and DNA capture device (B) as shown in FIG. 6.
Figure 10:
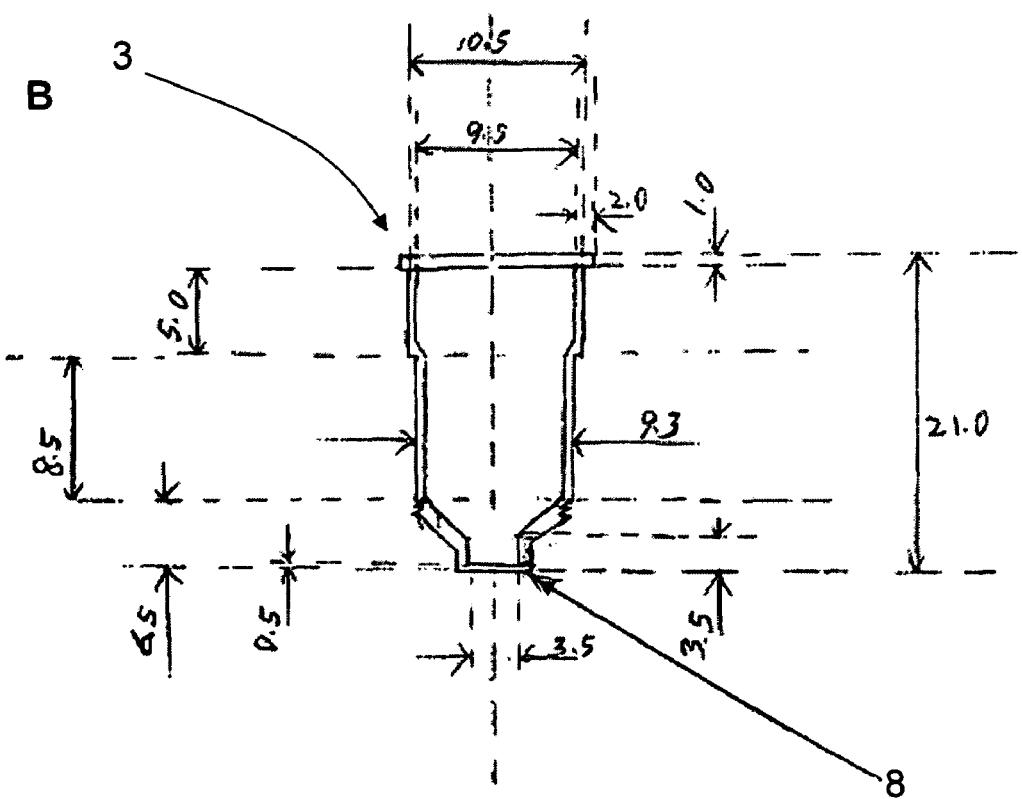

Drawings of a prototype lysate filtration device 2 and a prototype DNA-capture device 3 are shown in FIGS. 10A and 10B, respectively (dimensions in mm). A drawing of a preferred centrifuge tube 4 is shown in FIG. 9 (dimensions in mm). The centrifuge tube 4 contacts the bottom of the centrifuge rotor (i.e., bottoms-out in the rotor), such that the centrifuge tube 4 does not separate from the DNA-capture device during centrifugation. In some embodiments, the centrifuge tube 4 snaps or screws onto the DNA-capture device 3, such that the components of the apparatus do not separate in the rotor upon centrifugation. This later arrangement also facilitates the removal of the intact apparatus (e.g., as shown in FIG. 6C) from the centrifuge. The apparatus allows plasmid DNA to be captured on a DNA binding matrix in a little as a single centrifugation step.

In other embodiments the device may be adapted for use with an 8-well strip, 24, 48, 96, or 384-well plates, microarray, or other high throughput devices or formats.

C. Combined DNA Isolation Apparatus

Figure 7:
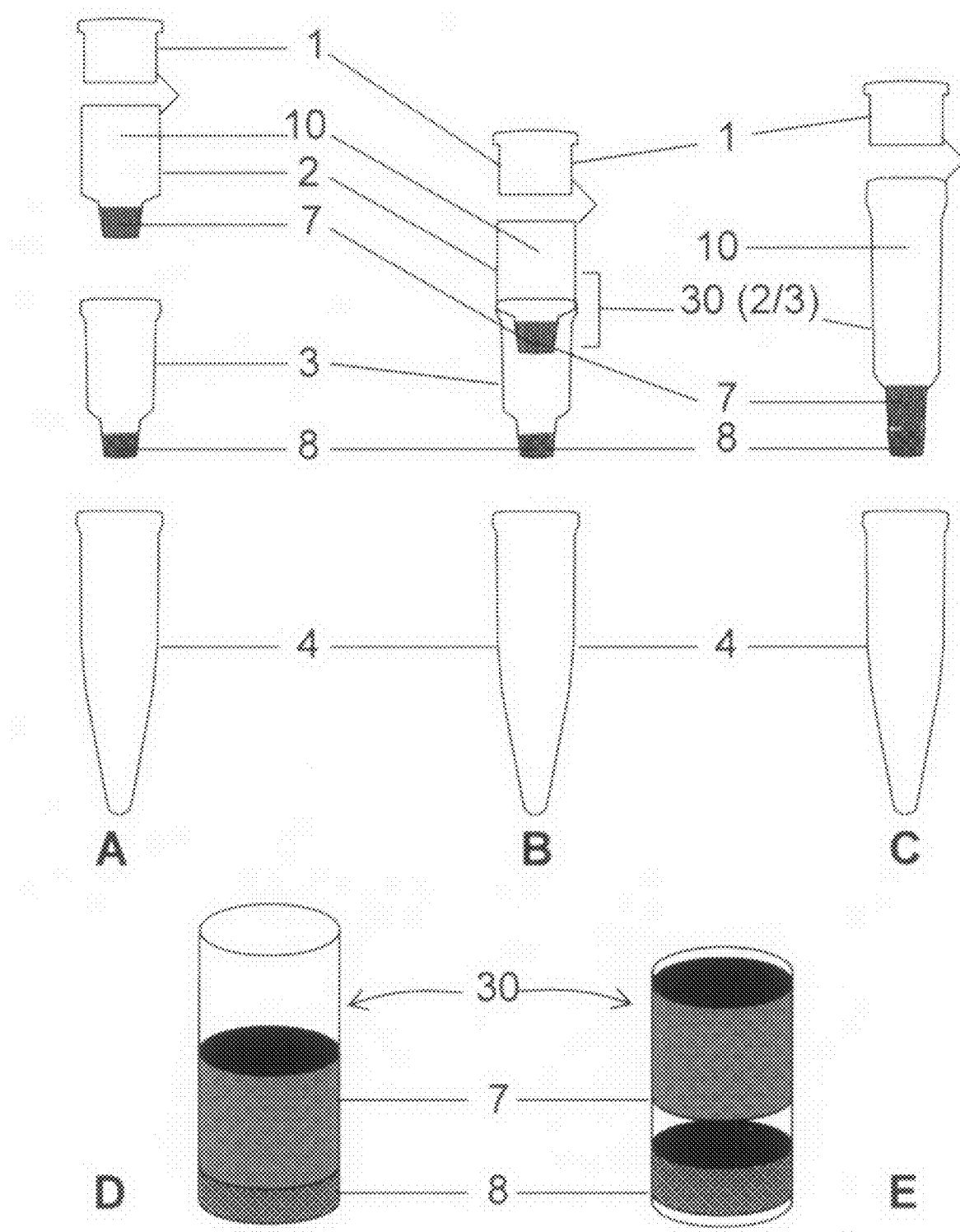
FIG. 7: Diagram and photograph depicting different embodiments of the invention, in which the lysate filtration device and DNA capture device are (A) discrete assemblies, (B) a combined assembly produced by assembling the lysate filtration device and DNA capture device, and (C) a combined assembly in which the filtering medium and the DNA binding matrix are in a combined DNA isolation apparatus that is functionally equivalent to an apparatus comprising a separate lysate filtration device and DNA capture device.

While FIG. 6 depicts an apparatus in which the lysate filtration device and DNA capture device are discrete components, these components can be a single assembly (e.g., assembled from discrete components, or manufactured as a single assembly). Examples of these apparatus are shown in FIG. 7. FIG. 7A shows an apparatus with a separate lysate filtration device 2 and DNA capture device 3. FIG. 7B shown an apparatus in which the lysate filtration device 2 and DNA capture device 3 are a combined DNA isolation assembly (or apparatus) 2/3, or 30. FIG. 7C shows an apparatus wherein the filtering medium 7 and the DNA binding matrix 8 are in a combined DNA isolation apparatus 30, which is functionally equivalent to an apparatus comprising a separate lysate filtration device 2 and DNA capture device 3. FIGS. 7D and 7E show apparatus wherein the filtering medium 7 and the DNA binding matrix 8 are in a combined DNA isolation assembly 30, which is the form more suitable for multi-well formats and high-throughput screening.

The combined DNA isolation assembly 30 comprises filtering medium 7, a DNA binding matrix 8 and a mixing chamber 10, of any volume. The mixing chamber may be larger if the DNA isolation assembly 30 is used to prepare large amounts of plasmid DNA, as in the case of a large-scale plasmid preparation. The volume of the mixing chamber may also be smaller, e.g., in the case of multi-well or high-throughput screening formats, where the bacterial alkaline lysate is likely to be delivered to the mixing chamber via an external apparatus, such as a multi-channel pump or microfluidic transfer device.

As further shown in FIGS. 7D and 7E, the filtering medium 7 and the DNA binding matrix 8 may be juxtaposed in the DNA isolation assembly 30 or separated by some volume. The filtering medium 7 and the DNA binding matrix 8 should be in fluid contact.

Most embodiments of the invention shown in the Figures show a spin-column apparatus for use in microfuge. However, as shown in FIG. 12, the apparatus of the invention need not be used in combination with a centrifuge. FIG. 12A depicts an embodiment of the invention for use with a vacuum source, which could be a vacuum manifold, vacuum line, etc. FIG. 12B depicts an embodiment of the invention for use with a positive pressure source. FIG. 12C depicts an embodiment of the invention for use with positive and/or negative pressure in an in-line format. FIG. 12D is similar to FIG. 12C but depicts an embodiment of the invention for multi-well applications or arrays, as shown in FIGS. 7D and 7E.

D. Colored Dyes and pH Indicators

In some embodiments of the invention, a pH-sensitive colored indicator is provided in the lysate filtration device, mixed with the P2 and/or P3 reagent, or added to the cell suspension. The colored indicator allows the user to visualize the pH of the cell suspension in the mixing chamber to monitor the progress of the lysis and neutralization steps.

Almost any pH indicator that changes color between a pH of about 4 and a pH of about 10, or any combination of indicators, can be used. Useful indicators include but are not limited to phenol red, m-cresol purple, cresol red, neutral red, bromophenol blue, bromothymol blue, thymol blue, phenophthalein, o-cresol phthalene, methyl red, methyl orange, methyl yellow, methyl green, methyl violet, thymolphthalein, alizarin yellow, bromocresol green, bromocresol purple, crystal violet (gentian violet), eosin Y, fuchsin, methylene blue, o-cresol red, orange G, safranin, oxylene cyanol, litmus, and red cabbage pigment.

Phenol red is an example of an indicator for use with the invention. In the presence of a small amount of phenol red, the bacterial suspension appears red in the basic environment of an alkali P2 reagent but turns yellow upon neutilization with a P3 reagent. In this manner, the end user can monitor the progress of the alkaline lysis procedure and determine when complete lysis and neutralization has occurred.

In most embodiments, RNase is added to the alkaline lysate to digest bacterial RNA. In a preferred embodiment, the RNase is RNase A. RNaseA is readily provided in a P2 and/or P3 reagent. In one embodiment, RNase A is added to a liquid P3 reagent. In another embodiment, dry RNase A is mixed with a solid P3 reagent. The time and manner of addition of RNase A is not critical.

E. Modified P2 Reagents

Conventional P2 reagents contain NaOH and SDS and may be used in either liquid or dry form, depending on the embodiment of the invention. Both NaOH and SDS are supplied and stored as dry chemicals, therefore conventional P2 reagents are readily provided in solid form. In embodiments of the invention wherein the P2 reagent is a liquid, it is desirable to minimize the volume of the P2 reagent necessary to lyse and particular volume of a bacterial suspension. Since the volume of the mixing chamber is finite, reducing the volume of the P2 reagent allows the use of a greater volume of bacterial suspension, which comprises more plasmid or similar DNA. Reducing the volume of the P2 reagent also facilitates handling and storage of the solution. Because conventional P2 reagents are already concentrated solutions, significantly reducing the volume leads to precipitation.

A feature of the invention is the use of modified a modified P2 reagent comprising NaOH (or another metal hydroxide), SDS, and isopropanol. Isopropanol reduces precipitation and allows the P2 reagent to be provided in more concentrated form (i.e., as a more concentrated liquid). P2 Reagents for use with the invention may also contain EDTA, e.g., to assist in lysing/disrupting bacterial membranes. A particular modified P2 reagent contains 0.8 M NaOH, 5% SDS, 5 mM EDTA, and 7% isopropanol. These amounts are not critical. 1-10% isopropanol is sufficient to reduce precipitation. Examples of suitable amounts include 1, 2, 3, 4, 5, 6, 7, 8, 9, and 10%. Even quantities of about 15 or 20% do not adversely affect plasmid recovery. Similar alcohols, such as 1-propanol and ethanol, can replace isopropanol in similar amounts. The amounts of NaOH and SDS are not critical and similar amounts are expected to produce acceptable results (e.g., about 0.2 N to about 2 N NaOH, and preferably about 0.5 N to about 1 N NaOH; and about 1% to about 10% SDS, and preferably about 3% to about 7% SDS, or saturation).

For the same amount of a given cell suspension, a reduced volume of this modified P2 is required compared to a conventional P2 reagent. For example, while conventional minipreps use about equal volumes of P1 and P2 reagent solutions; a sufficient amount of modified P2 can be provided in only about ⅛ the volume of the suspended cells (e.g., about 800 µl cells and about 100 µl modified P2). Note that these ratios/volumes are examples and are not to be construed as limiting.

In the commercial embodiment of the invention, the modified P2 reagent is supplied as 7× concentrate (Example 1). However, this modified P2 reagent concentrate can be used as a 1.5× to 15× concentrate with acceptable results. The concentrate can be added directly to a cell suspension, avoiding the conventional steps of recovering the bacteria from a bacterial suspension (usually via centrifugation) and resuspending the resulting bacterial pellet in a P1 reagent.

The modified P2 reagents of the invention may be used in combination with conventional P3 reagents and conventional methods, or with the embodiments of the modified P3 reagents and methods, described herein. Conventional methods include removing the flocculent bacterial debris from an alkaline lysate by filtration (e.g., using a spin-column filtration apparatus), or by centrifugation to pellet the debris. The resulting lysate filtrate (i.e., clarified supernatant, filtrate, or flow-through) are then transferred to a separate vessel or apparatus having a DNA binding matrix for capturing the DNA.

F. Modified P3 Reagents

The invention provides a modified P3 reagent comprising a chaotropic agent to increase plasmid DNA binding to the DNA binding matrix. Preferred chaotropic agents include guanidinium-HCl, guanidinium isothiocyanate, sodium iodide, potassium iodide, perchlorate, and trichloroacetate. The modified P3 reagent may also comprises potassium chloride, or other potassium salts, such as potassium acetate.

Where the modified P3 reagent is provided in solid or immobilized form, it further comprises a solid acid to replace the liquid acid normally present (i.e., acetic acid). Preferred solid acids include malic acid and citric acid; however, other acids (malonic, maleic, succinic, tartaric, pyruvic, and similar acids) are expected to work with the invention. A particular modified P3 reagent dry mix formulation is 16.2 g KCl, 3.09 g malic acid, 16.5 g guanidine-HCl, and 2 mg RNase A. These values and ratios are approximate and not critical.

Other modified P3 reagent formulation will work with the invention. As noted elsewhere, RNase A is preferably added to the P3 reagent but may optionally or additionally be added to the cell suspension, to the P2 reagent, to the mixing chamber (including the cap), or at any convenient opportunity, preferably prior to capturing the DNA on the DNA binding matrix.

The modified P3 reagents of the invention may be used in combination with conventional P2 reagents and conventional methods, or with the embodiments of the modified P2 reagents and methods, described herein. Conventional methods include removing the flocculent bacterial debris from an alkaline lysate by filtration or centrifugation.

G. Solid or Immobilized Reagents

Some embodiments of the invention are used in combination with solid or immobilized P2 and/or P3 reagents in place of liquid reagents. Other embodiments combine liquid and solid reagents. As used herein, solid refers to dry solid or semi-solid compositions and formulations that would serve to immobilize the P2 and/or P3 reagent(s) for several months at room temperature. The solid reagents should be stable under typical room temperature storage conditions. High viscosity liquid formulations of P2 and/or P3 may also be used to practice the invention, provided that P2 and/or P3 reagents remains substantially immobilized within the mixing chamber during transport and storage of the apparatus to the end-user.

Methods for coating surfaces with dry compositions are well known in the art, and include drying (e.g., spray-drying and freeze-drying) the P2 and/or P3 reagent compositions on the inside surface of the mixing chamber in the lysate filtration device and/or sealing cap. Dry reagents may also be provided as tablets. A binder, adhesive, or other additive may be used, so long as the formulation does not interfere with the alkaline lysis process or recovery of plasmid DNA (see, e.g., *Remington: The Science and Practice of Pharmacy*-21st Edition. University of the Sciences in Philadelphia (Ed.). (2005) Lippincott Williams & Wilkins). Formulations should be water-soluble to dissolve in the cell suspension.

Dry or formulated chemicals can be also be provided in a water-soluble package or provided under or a behind a water-soluble protective barrier or film. As used herein, water-soluble polymers include polymers that are technically "sensitive to the presence of water," rather than water-soluble. Useful films include polyethylene/vinyl alcohol, polyacrylate, polyurethane, polyesters hydrogels, polylactides, ethylene vinyl acetate, ethylene vinyl alcohol, poly-D-(-)-3-hydroxybutyric acid, degradable lactic acid-glycolic acid copolymers, copolymers of L-glutamic acid and gamma ethyl-L-glutamate, poly (2-hydroxyethyl-methacrylate), crosslinked polyethers including cross-linked poly(ethylene oxide), carboxymethylcellulose, hydrocolloid type materials, cellulose acetate, and phthalate.

Dry chemicals can also be suspended or dispersed in a water-soluble, semi-solid admixture (e.g., a paste, gum, grease, or similar form), as long as the underlying carrier or polymer does not interfere with the alkaline lysis process or recovery of the plasmid DNA. Ideally, the formulation should be of sufficient character and viscosity to immobilize the P2 and/or P3 reagent to facilitate storage and handling prior to addition of the cell suspension (typically by the end user).

In embodiments where both P2 and P3 are provided in solid or immobilized form, the P2 reagent should dissolve before the P3 reagent. In particular, the P2 formulation should dissolve upon contact with a cell suspension, while the P3 formulation should dissolve a number of seconds (e.g., 30, 60 or more) after the P2 formulation has been released, dissolved, and dispersed sufficiently to lyse the bacteria.

These times are exemplary and are not to be construed as limiting. Shorter delays, e.g., for automated processing, or longer delays, e.g., to provide additional time for mixing and handling, may be preferable to the end-user.

Other methods and techniques for depositing dry or semi-solid chemical compositions are known in the art and are not part of the principle invention. The reader should give the terms solid and immobilized form their broadest interpretation.

H. Comparison of the Present Invention with Conventional Methods

Figure 11:
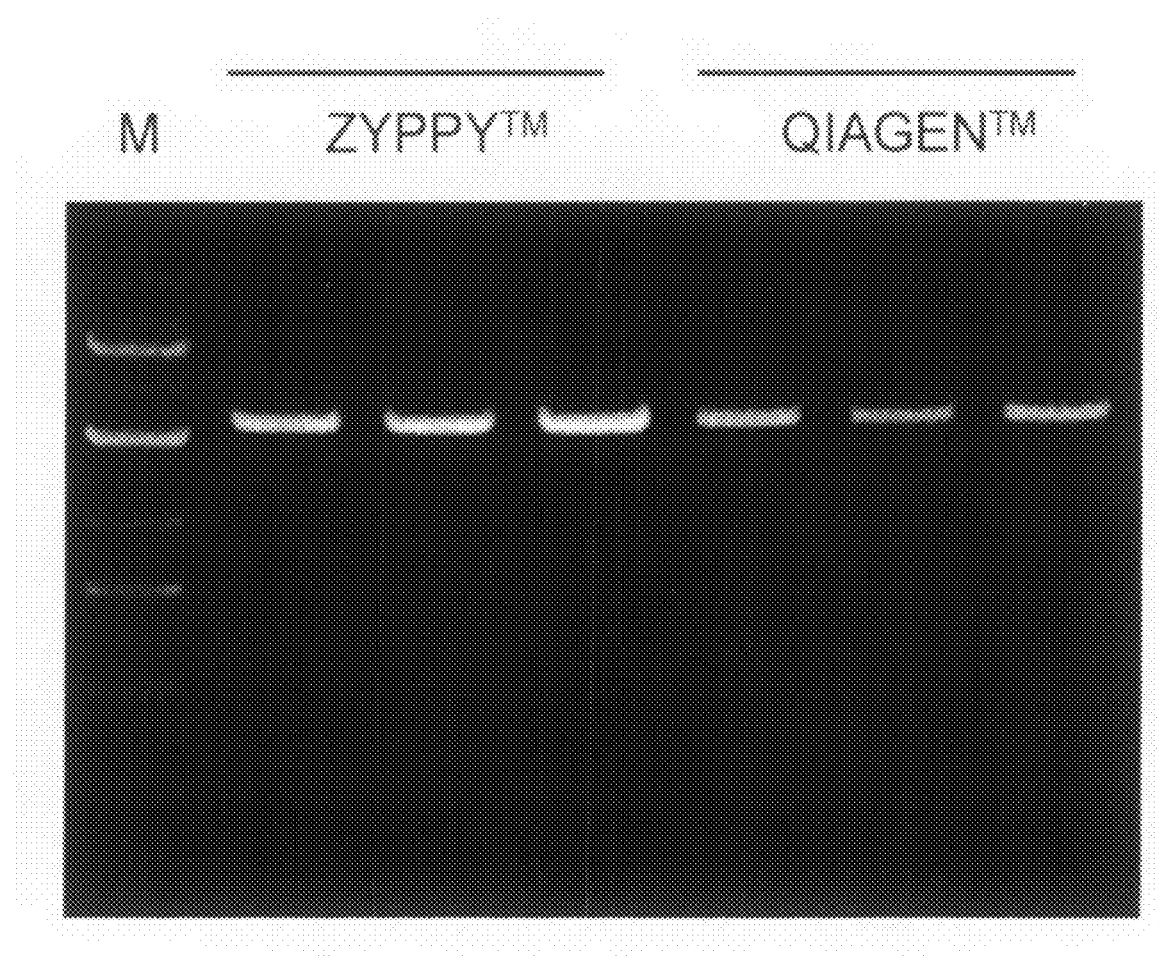
FIG. 11: Comparison of a kit of the present invention with conventional methods. Plasmid DNA was prepared using either the embodiment of the invention described in Example 1 or a QUIAGEN™ kit.

FIG. 11 shows the results of a comparison of the methods and apparatus of the present invention with conventional methods and apparatus. Plasmid DNA (PGEM®; Promega, Madison, Mich., USA) was isolated from 600 µl of *E. coli* in growth medium using the ZYPPY™ Plasmid Miniprep Kit described in Example 1 or a kit supplied by another supplier (QUIAGEN) and using the suppliers instructions. Isolated and eluted plasmid DNA was digested with EcoRI and resolved on an agarose gel. The marker is the 1 kb DNA Marker from New England Biolabs. The comparison was performed in triplicate.

The ZYPPY™ Plasmid Miniprep Kit includes an apparatus similar to that shown in FIG. 6, a modified liquid P2 reagent comprising an alcohol to allow it to be supplied in concentrated form, and a modified liquid P3 reagent comprising a chaotropic agent. The ZYPPY™ Plasmid Miniprep Kit produced an improved yield of better quality DNA than the other supplier's kit, while requiring fewer steps and less manipulation.

I. Definitions

Scientific terms have generally been given their ordinary meaning as used in the art. The following inventions are provided for clarity:

Added directly: With respect to the addition of P2 to a bacterial suspension, added directly means that prior concentration of the bacteria by centrifugation or filtration is not necessary. The modified P2 reagents can simply be added to a volume of bacterial culture medium (e.g., from an overnight E. coli culture).

Alkaline lysate: A bacterial suspension following treatment with P2 and P3. Plasmid DNA in an alkaline lysate has been denatured and renatured.

Assembly/assemblies: Discrete parts or components as in as product for delivery to an end user. The parts or components may be assembled with other parts as provided to the end user but are not further dismantled or broken into smaller or more numerous parts in the normal course of using the apparatus.

Bacterial suspension: Bacteria in medium, lysis buffer (i.e. P1), water, or another liquid reagent that does not interfere with the steps of alkaline lysis. The bacterial suspension may be directly from a culture or may the result of centrifugation and resuspension of bacteria from a culture, plate, stab, slant, contaminated water specimen, biological warfare specimen, or other sample comprising or suspected of comprising bacteria having plasmid DNA Binding the plasmid DNA to the DNA-binding matrix: Incubating a solution or suspension comprising plasmid DNA (e.g. an alkaline lysate) in the presence of DNA binding matrix, such as a silica-based matrix, such that plasmid DNA binds to the DNA-binding matrix. A chaotropic agent, such as sodium iodide or guanidinium-HCl is usually present to increase binding efficiency. The plasmid DNA may then be eluted from the DNA-binding matrix using an aqueous solution, such as water or Tris-acetate buffer (TE). As used herein, the expression binding the plasmid DNA to the DNA-binding matrix is synonymous with capturing the plasmid DNA.

Combined with: Mixed, added in addition to, added together with, added as part of a bulk mixture to, or otherwise brought together.

Contact the DNA-binding matrix: To physically contact a DNA-binding matrix, as when a liquid, such as an alkaline lysis lysate comprising or suspected of comprising plasmid DNA, is passed over a DNA binding matrix in a column or incubated in the presence of DNA binding matrix on beads or another solid matrix.

Filtering medium: A matrix suitable for trapping insoluble particle present in an alkaline lysate, including paper filters, cheesecloth, and similar bulk filter materials used to make column frits. Many materials may be used to practice the invention but cost, consistency, and stability should be considered.

Fluid contact: Arranged so as to allow fluid to flow from one device to another as described herein and as understood in the art. Fluid contact is synonymous with the phrase fluid communication.

Films: Flexible films are typically planar forms of plastics, which should be thick enough to support and retain a solid or immobilized composition. Films include single layer polymers and multilayer structures. Water-soluble films may include tie layers and copolymers. Films should be soluble in P2 and/or P3 buffer as appropriate. Release times can be tailored by polymer selection and film thickness. Examples of materials suitable for use with the invention include but are not limited to polyacrylate, polyurethane, and other polyesters hydrogels, polylactides, ethylene vinyl acetate, ethylene vinyl alcohol (EVOH, including ethylene vinyl alcohol copolymers), vinyl acetate, poly-D-(-)-3-hydroxybutyric acid, degradable lactic acid-glycolic acid copolymers, copolymers of L-glutamic acid and gamma ethyl-L-glutamate, poly (2-hydroxyethyl-methacrylate), crosslinked polyethers including cross-linked poly(ethylene oxide), carboxymethylcellulose, hydrocolloid type materials, and other material.

Isolate plasmid DNA: To remove bacterial debris, salts, and other contaminants, to an extent sufficient to permit the use of the plasmid DNA in standard laboratory DNA manipulations and assays, such as sequence analysis, PCR analysis, methylation analysis, among other assays. The quality of the plasmid DNA isolated using the methods, apparatus, and reagents described herein is similar to that obtained using conventional alkaline lysis coupled to spin-column methods.

Lysate filtrate: A bacterial suspension following treatment with P2 and P3 and subsequent filtration (or centrifugation) to remove genomic DNA and aggregated bacteria proteins. Lysate filtrate comprises plasmid DNA unless it has been in contact with a DNA-binding matrix, in which case it is depleted of plasmid DNA.

Plasmids: Plasmids are (typically) circular double-stranded DNA molecules distinct from the bacterial chromosomal DNA and capable of autonomous replication. Plasmid DNA is often called vector DNA. As used herein, plasmid DNA includes all epimeric forms of DNA that can be propagated in bacteria (e.g., plasmids, phagemids, cosmids, shuttle vectors, expression vectors, gene therapy vectors, and the like).

Provided in: Positioned, placed, presented, disposed, stored, sequestered, isolated, contained, or made available in. This expression is used with reference to P2 and/or P3 reagents, which may be provided in the mixing chamber where they contact a bacterial suspension according to the methods of the invention. The P2 and or/P3 reagents may be provided in solid or immobilized form (as described, herein), in liquid form, or a combination, thereof, depending on the particular embodiment of the invention.

Single centrifugation step: Requiring no more than one centrifugation event at an appropriate speed, i.e., a single acceleration and deceleration cycle or one "spin" in a centrifuge. The centrifugation event may require several minutes. Shorter times are preferred, for example, less than a minute, less than 30 seconds, less than 15 seconds, or even less than 5 seconds.

Single centrifugation or pressure step: Requiring no more than a single centrifugation step (see, above), and/or a single application of positive or negative gas or fluid pressure force, so as to cause the alkaline lysate to flow in the direction of the DNA binding matrix. Negative pressure may be applied using a vacuum manifold, as used in combination with commercially-available "miniprep" apparatus and kits. Vacuum or positive pressure may also be supplied via tubing (including capillary and microcapillary tubing), a pressurized chamber, a manifold, a microfluidic apparatus, or a similarly acting devices. Pressure is typically air pressure but liquid pressure, or combinations of air and liquid pressure, may be preferable for manipulating small volumes.

Solid or immobilized: Solid refers to a P2 and/or P3 reagent that is provided in solid or semi-solid form. Solid forms include granules, crystals, powders, chalks, and other solid forms. Semi-solid forms include pastes, creams, gels, ointments, colloidal suspensions, and like compositions. The solid and semi-solid forms may include any number or binders or additives, provided that they do not interfere with the process of alkaline lysis or plasmid DNA-binding to the solid matrix. Examples of binders and additives are found in Remington (supra). Immobilized refers to a P2 and/or P3 reagent that remains substantially confined or localized to a portion of the mixing chamber until it dissolves in a bacterial suspension (including a bacterial suspension to which P2, RNase, dye, or other component. has been added). Unless otherwise indicated by context, solid or immobilized means solid and/or immobilized. By contrast, a liquid P2 or P3 reagent, as used in conventional methods of plasmid DNA preparation, is neither solid, nor immobilized.

Solid and semi-solid P2 and/or P3 reagents may be immobilized in the lysate filtration device or in the sealing cap, depending on the embodiment of the invention. Solid reagents may be immobilized by being dried (including freeze and spray-dried) onto a surface in the mixing chamber. Solid forms may be applied to a surface in the mixing chamber using an adhesive that does not interfere with the methods of the invention. Semi-solid forms may be immobilized by virtue of their tendency to adherence to surfaces, in which case they are spread, injected, dropped, or otherwise applied to a surface in the mixing chamber. Semi-solid formulations may be heated or diluted in a solvent prior to their application.

Solid or semi-solid P2 and/or P3 reagents may be immobilized in or behind water-soluble films, barriers, or packages. As used herein, the term water-soluble encompasses films that are, technically, sensitivity to water, or otherwise dissolve in an aqueous bacterial suspension in a manner that is chemically distinct but functionally equivalent to water-solubility. Films may be used to cover a solid or semi-solid P2 or P3 reagent, in which case the edges and or corners or a sheet of film are glued or mechanically attached such that the P2 or P3 reagent is substantially immobilized or localized at a predetermined portion of the mixing chamber. Films may also be used to package (i.e., wrap, envelope, encase, or enclose) solid or semi-solid reagents, in which cases the packages may be placed in the lysate filtration device or sealing cap.

Solid or semi-solid P2 and/or P3 reagents may also be immobilized behind insoluble or physical barriers (e.g., sieves, gratings, perforations, or restrictor plates, or similar restraints.), so long as the P2 or P3 reagents are substantially immobilized or localized in the mixing chamber and are in fluid contact with the bacterial suspension so as to facilitate dissolution and thorough mixing of the reagent(s) in/with the bacterial suspension. Physical barriers can be combined with soluble barriers (e.g., to permit the use of a thinner or less robust film).

Solid acid: An acid that is solid at room temperature. A solid acid can be an acidic salt. Examples include malic, malonic, maleic, succinic, tartaric, citric, pyruvic acid, mono or disodium citric acid, and similar compounds. These acids are distinguishable from acetic acid, which is a liquid a room temperature. Preferred solid acids are stable for many months at room temperature, inexpensive, non-hygroscopic, and readily available. Other examples of solid acids are described in Remington (supra).

Spin-column apparatus: Columns for use in standard centrifuges, microfuges, vacuum-manifolds, or low or high-pressure (HPLC, HPCE) systems, all of which are known in the art. A single column means an individual chromatographic column, for example a discrete spin-column, vacuum column, gravity-flow column. Multi-well formats may also be used, wherein each well operates as a single column. The column preferably includes a narrow, tapered neck where filter material (in the case of the lysate filtration device) or, e.g., a silica resin material (or matrix; in the case of the DNA-capture device) is contained. A tapered neck in combination with a small amount of DNA-binding material facilitates efficient elution and recovery of plasmid DNA.

Substantially confined or localized to: Confined or localized sufficiently so as not to interfere with alkaline lysis and plasmid DNA recovery according to the particular embodiment of the invention. Solid or immobilized P2 and/or P3 reagents should remain in a predetermined portion of the mixing chamber throughout shipping and storage, until the end user adds bacterial suspension; however, minor leakage, migration, or contamination or reagents (e.g., less than about 2% or even less than 5%) is unlikely to interfere with the methods and apparatus described herein.

G. Utility

As plasmid DNA preparation remains a necessary and important laboratory procedure, the present invention is of readily apparent value to researchers and technicians. The apparatus and methods of the invention will allow the rapid and efficient screening of large numbers of plasmids (e.g., from transformed bacteria). In addition to saving time and effort, the apparatus and methods of the invention will allow researchers to identify rare or infrequent plasmids, such as those resulting from complicated cloning schemes, those comprising toxic genes subject to deletion and rearrangement, and those harboring nucleotide sequence that are under-represented in a population (e.g., a population of PCR products).

The invention may be especially useful for field workers, who have limited access to laboratory supplies and equipment or require a rapid method and apparatus for isolating plasmid or similar DNA. Field workers include epidemiologists, virologists, and medical personal. Military specialists could also benefit from use of devices and methods of the present invention.

The invention is well suited to be supplied in a kit form with the spin-column/vacuum apparatus, appropriate reagents, and instructions for use. Such kits will typically comprise embodiments of the apparatus described, herein; conventional P2 and P3 buffers or the modified buffers described herein; and instructions.

Kits are particularly useful in the field for isolating of DNA from samples and organisms at source locations. These include labile samples not amenable to transport or laboratory culture. Kits of parts for performing the methods of the invention are particularly useful for identifying plasmid-carrying bacteria in hospitals (including military and other field hospitals), at sites of natural disasters, terrorist attacks, and other catastrophic events, in contaminated water and food supplies, in patient and/or corpse biopsy or pathological samples (e.g., blood, feces, urine, sputum, seminal and vaginal fluids, or other bodily fluids). Kits may also be used to identify biological warfare agents comprising bacteria (e.g., the anthrax *bacillus*) that harbor plasmid-borne determinants of pathogenesis. Kits are also useful in the laboratory, where plasmid DNA preparation is a standard procedure.

The embodiments of the invention described herein are merely exemplary and should not be construed as limiting. One skilled in the art will appreciate additional embodiments and modifications upon reading the disclosure.

All reference cited herein are hereby incorporated by reference in their entirety. The embodiments of the invention described herein are provided as examples. The following examples are provided to further illustrate the invention.

Additional aspects of the invention will be apparent to one skilled in the art without departing from the scope of the invention.

EXAMPLES

Example 1

Commercial Embodiment of the Invention

The following description is taken directly from the instruction manual of the first commercial kit for practicing the present invention. This commercial kit represents only one embodiment of the invention. Future commercial kits are likely to feature other embodiments, including solid or immobilized P2 and/or reagents.

ZYPPY™ Plasmid Miniprep Kit

The ZYPPY™ Plasmid Miniprep Kit features a PELLET-FREE™ modified alkaline lysis method that bypasses the initial centrifugation and resuspension steps common to classical miniprep procedures. The 7× Lysis Buffer is added directly to a bacterial culture, neutralized, then DNA is isolated using silica matrix-based spin-column technology. The included color-coded buffers permits easy visualization and rapid assessment of complete bacterial cell lysis The ZYPPY™ Plasmid Miniprep Kit is the fastest and simplest method available to efficiently separate plasmid DNA from chromosomal DNA and cellular RNA. The plasmid DNA purified using our kit is of the highest quality and is well suited for use in bacterial transformation, restriction endonuclease digestion, DNA ligation, PCR, transcription, sequencing, and other sensitive downstream applications. The device supplied in the kit is similar to that shown in FIG. 6.

Specifications

DNA Purity: Plasmid DNA is well suited for ligation, sequencing, restriction endonuclease digestion, in vitro transcription, and other sensitive applications requiring pure DNA. Typical Abs 260/280 index is $\geq 1.8$.

Plasmid DNA Yield: Up to 25 μg per preparation, depending on the plasmid copy number, culture growth conditions, and strain of $E.\ coli$ utilized.

Plasmid DNA Size: Up to 25 kb.

Recovery Volume: $\geq 30$ μl.

Procedure: Performed at room temperature (15-30° C.).

Buffer Preparation

1. Add the RNase A to the Neutralization Buffer and store the constituted buffer at 4-8° C. The final concentration of RNase A will be 100 μg/ml (D4036) or 50 μg/ml (D4019 & D4020).

2. Add 24 ml of 100% ethanol (26 ml of 95% ethanol) to the 6 ml ZYPPY™ Wash Buffer concentrate (D4036), 48 ml of 100% ethanol (52 ml of 95% ethanol) to the 12 ml ZYPPY™ Wash Buffer concentrate (D4019), or 192 ml of 100% ethanol (208 ml of 95% ethanol) to the 48 ml ZYPPY™ Wash Buffer concentrate (D4020) before use.

Protocol

The following procedure is performed at room temperature.

1. Add 6001 of bacterial culture grown in LB medium to a 1.5 ml microcentrifuge tube. Alternatively, centrifuge up to 3 ml of bacterial culture in a 1.5 ml conical tube for 30 seconds at 11,000-16,000×g. Discard the supernatant. Add 600 μl of TE or water to the bacterial cell pellet and completely resuspended by vortexing or pipetting.

2. Add 100 μl of 7× Lysis Buffer (Blue) to 1-10 samples and mix by inverting the tube 4-6 times. Proceed to step 3 within 2 minutes. Excessive lysis can result in denatured plasmid DNA. If processing a large number of samples, we recommend working with groups of ten or less at a time. Continue with the next set of ten samples after the first set has been neutralized and mixed thoroughly.

3. Add 350 μl of cold Neutralization Buffer (Yellow) and mix thoroughly, but do not vortex. The sample will turn yellow when the neutralization is complete and a yellowish precipitate will form. Invert the sample an additional 2-3 times to ensure complete neutralization. Ensure that RNase A has been added to the Neutralization Buffer.

4. Centrifuge at 11,000-16,000×g for one minute.

5. Transfer the supernatant (~900 μl) into the provided ZYMO-SPIN™ II column. Avoid disturbing the cell debris pellet.

6. Place the column into a Collection Tube and centrifuge at for 15 seconds.

7. Discard the flow-through and place the column back into the same Collection Tube.

8. Add 200 μl of Endo-Wash Buffer to the column. Centrifuge for 15 seconds. It is not necessary to empty the collection tube.

9. Add 400 μl of ZYPPY™ Wash Buffer to the column. Centrifuge for 30 seconds. Ensure that RNase ethanol has been added to the concentrated ZYPPY™ Wash Buffer.

10. Transfer the column into a clean 1.5 ml microcentrifuge tube then add 30 μl of ZYPPY™ Elution Buffer directly to the column matrix and let stand for one minute at room temperature. The ZYPPY™ Elution Buffer contains 0.1 mM EDTA. If required, pure water (neutral pH) can also be used to elute the DNA 11. Centrifuge for 15 seconds to elute the plasmid DNA.

The DNA is suitable for immediate use.

What is claimed is:

1. A spin-column apparatus for isolating plasmid DNA from a bacterial alkaline lysate, the apparatus comprising a lysate filtration device having a mixing chamber for an alkaline lysate, and having filtering medium in fluid contact with the mixing chamber, wherein a concentrated P2 reagent solution and dry formulation P3 reagent is are disposed in the mixing chamber above the filtering medium; the lysate filtration device being in fluid contact with a DNA capture device having a DNA binding matrix; and wherein the DNA binding matrix is capable of substantially purifying plasmid DNA from cellular components.

2. The apparatus of claim 1, wherein the lysate filtration device further comprises a sealing cap, and the lysate filtration device and sealing cap together form the mixing chamber.

3. The apparatus of claim 2, wherein the lysate filtration device and the DNA capture device are separate assemblies that are in fluid contact.

4. The apparatus of claim 2, wherein the lysate filtration device and the DNA capture device are a combined assembly.

5. The apparatus of claim 1, in a multi-well format.

6. The apparatus of claim 1, wherein the P2 reagent further comprises an alcohol.

7. The apparatus of claim 6, wherein the alcohol is selected from isopropanol, 1-propanol, and ethanol.

8. The apparatus of claim 6, wherein the P3 reagent further comprises a chaotropic agent.

9. The apparatus of claim 8 wherein the P3 reagent further comprises a solid acid.

10. The apparatus of claim 8, wherein the P2 reagent or P3 reagent contains a pH indicator.

11. A spin-column apparatus for isolating plasmid DNA from a bacterial alkaline lysate, the apparatus comprising a mixing chamber for an alkaline lysate in fluid contact with first a filtering medium, and then a DNA binding matrix; wherein an immobilized concentrated P2 reagent and an immobilized P3 reagent in a dry solid or semi-solid formulation are disposed in the mixing chamber above the filtering medium, free from absorbent media; the P2 reagent being disposed to contact and lyse a cell suspension producing an alkaline lysate before contacting the P3 reagent, wherein the filtering media and DNA binding matrix are permeable to the alkaline lysate upon centrifugation or application of pressure; and wherein the DNA binding matrix is capable of substantially purifying plasmid DNA from cellular components.

12. The spin column apparatus of claim 11, wherein the mixing chamber, filtering medium, and DNA binding matrix, are in a single column assembly.

13. The spin column apparatus of claim 11, wherein the mixing chamber and filtering medium are in a lysate filtering device and the DNA binding matrix is in a DNA capture device, and the lysate filtering device DNA capture device are in fluid contact.

14. The apparatus of claim 11, in a multi-well format.

15. The apparatus of claim 11, wherein the P2 reagent further comprises an alcohol selected from the group consisting of isoproponol, 1-proponol and ethanol.

16. The apparatus of claim 15, wherein the P3 reagent further comprises a chaotropic agent.

17. A kit of parts comprising a spin-column apparatus of claim 8, a concentrated P2 reagent, a dry formulation P3 reagent, and instructions.

18. The kit of parts of claim 17, wherein a dry formulation P2 reagent is substituted for the concentrated P2 reagent.

19. A lysate filtration device for filtering a bacterial alkaline lysate, the device comprising a mixing chamber, having a top and bottom opening, a P2 reagent disposed immobilized in the mixing chamber, the P2 reagent being about a 1.5× to 15× concentrated solution containing an alcohol, a P3 reagent disposed in the mixing chamber, the P3 reagent further comprising a potassium salt, a chaotropic agent, and a solid acid, the P3 reagent being a dry formulation, a filtering media positioned in the mixing chamber, the filtering media being separate from the P2 reagent and P3 reagent and in fluid contact with the mixing chamber, the mixing chamber being configured to receive a bacterial cell suspension through the top opening, wherein contact between the P2 reagent and the bacterial cell suspension can occur in the mixing chamber, whereby contact between the P2 and the bacterial cell suspension will result in a bacterial alkaline lysate, and wherein contact between the bacterial alkaline lysate and P3 reagent can occur in the mixing chamber, whereby contact between the P3 reagent and the bacterial alkaline lysate will result in a neutralized lysate, the neutralized lysate further comprising a flocculent bacterial debris and a remaining bacterial lysate, and wherein the filtering media is for filtering the flocculent bacterial debris, from the remaining bacterial lysate.

20. The apparatus of claim 1, wherein the dry formulation P3 reagent further comprises a potassium salt, a chaotropic agent, and a solid acid.

21. The apparatus of claim 20, wherein the chaotropic agent is selected from the group consisting of guanidinium-HCl, guanidinium isothiocyanate, iodide, perchlorate, and trichloroacetate.

22. The apparatus of claim 20, wherein the solid acid is selected from the group consisting of malic acid, citric acid, malonic acid, maleic acid, succinic acid, tartaric acid, and pyruvic acid.

23. The apparatus of claim 20, wherein the dry formulation P3 reagent is selected from the group consisting of tablets, powders, granules, crystals, chalks, films, pastes, gums, greases, and polymers.

24. The apparatus of claim 20, wherein the dry formulation P3 reagent consists of about 16.2 g KCl, about 3.09 g malic acid, about 16.5 g guanidine-HCl, and optionally about 2 mg RNase A.

25. The apparatus of claim 1, wherein the concentrated P2 reagent consists of about 0.5 N to about 1.0 N NaOH, about 1% to about 10% SDS (wt./vol.), about 5 mM EDTA, and about 1% to about 10% (vol./vol.) isoproponol.

26. The apparatus of claim 1, wherein the concentrated P2 reagent is a concentrate from about 1.5× to about 15×.

27. The apparatus of claim 1, wherein the concentrated P2 reagent is about a 7× concentrate.

28. The apparatus of claim 11, wherein the dry solid or semi-solid formulation P3 reagent is selected from the group consisting of tablets, powders, granules, crystals, chalks, films, pastes, gums, greases, polymers, creams, gels, ointments, and colloidal suspensions.

* * * * *